US00PP16137P2

(12) United States Plant Patent
Trees

(10) Patent No.: US PP16,137 P2
(45) Date of Patent: Nov. 29, 2005

(54) ***OSTEOSPERMUM* PLANT NAMED 'BALSERPINK'**

(50) Latin Name: *Osteospermum ecklonis*
Varietal Denomination: Balserpink

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 23 days.

(21) Appl. No.: 11/016,288

(22) Filed: Dec. 17, 2004

(51) Int. Cl.[7] ..... A01H 5/00
(52) U.S. Cl. ..... Plt./360
(58) Field of Search ..... Plt./360

*Primary Examiner*—Kent Bell
(74) *Attorney, Agent, or Firm*—Wood, Phillips, Katz, Clark & Mortimer

(57) ABSTRACT

A new and distinct cultivar of *Osteospermum* plant named 'Balserpink' characterized by its single inflorescence form with pink-colored ray florets and blue-colored disc florets, freely branching character, dark green-colored foliage, and compact and upright growth habit.

1 Drawing Sheet

Latin name of the genus and species of plant claimed: *Osteospermum ecklonis.*

Variety denomination: 'Balserpink'.

BACKGROUND OF THE INVENTION

The present invention relates to a new and distinct cultivar of *Osteospermum* plant botanically known as *Osteospermum ecklonis*, and hereinafter referred to by the cultivar name 'Balserpink'.

The new *Osteospermum* originated in a controlled breeding program in Arroyo Grande, Calif. during July 2002. The objective of the breeding program was the development of *Osteospermum* cultivars that are freely branching, have a compact and upright growth habit, are freely flowering, and have unique inflorescence coloration.

The new cultivar was the result of the open-pollination of the commercial variety of *Osteospermum ecklonis* 'Mira', U.S. Plant Pat. No. 11,082, characterized by its dark purple-colored ray florets with darker purple stripes and medium green-colored foliage. Seed from the above stated open-pollination was germinated and grown to maturity. One plant from within the progeny was discovered and selected by the inventor during November 2002 in a controlled environment at Arroyo Grande, Calif.

Asexual reproduction of the new cultivar by terminal stem cuttings since November 2002 at West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar have been repeatedly observed and can be used to distinguish 'Balserpink' as a new and distinct cultivar of *Osteospermum* plant:

1. Single inflorescence form with pink-colored ray florets and blue-colored disc florets.
2. Dark green-colored foliage.
3. Freely branching character.
4. Compact and upright growth habit.

Plants of the new cultivar differ from plants of the female parent primarily in inflorescence color and foliage color.

Plants of the new cultivar are most similar to the cultivar Akavol, not patented. However, in side-by-side comparisons, plants of the new cultivar differed from plants of 'Akavol' in the following characteristics:

1. Plants of the new cultivar are shorter than plants of 'Akavol'.
2. Plants of the new cultivar have shorter internodes than plants of 'Akavol'.
3. Plants of the new cultivar have different stem coloration than plants of 'Akavol'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describe the colors of the new cultivar. The plants were grown in 10 cm pots for 14 weeks in a greenhouse at West Chicago, Ill.

DETAILED BOTANICAL DESCRIPTION

Figure 1:
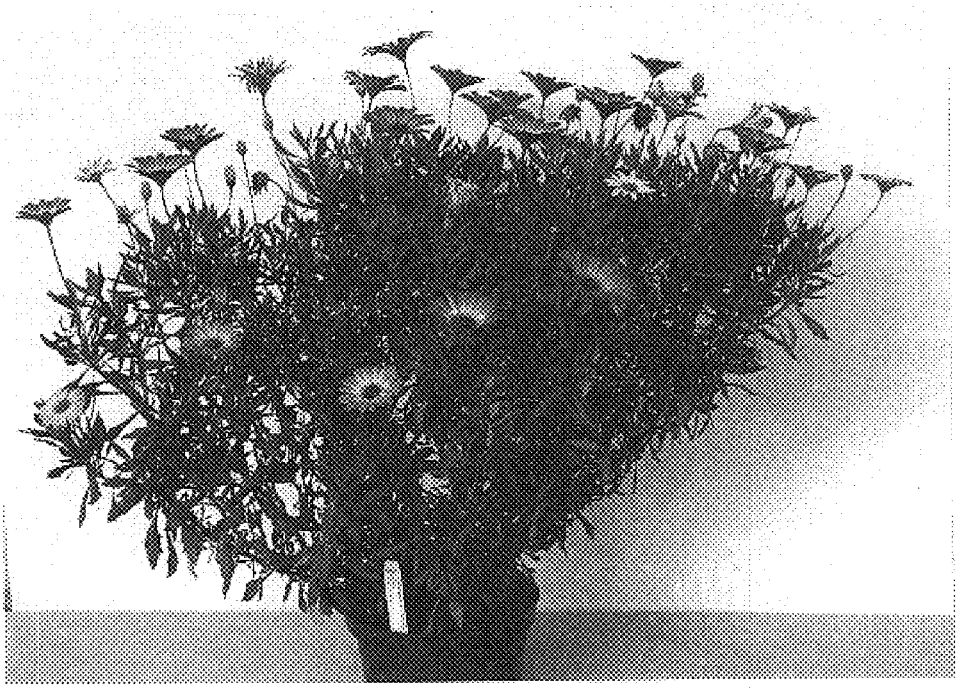
FIG. 1 illustrates a side view of the overall growth and flowering habit of the new cultivar with one plant per pot.
Figure 2:
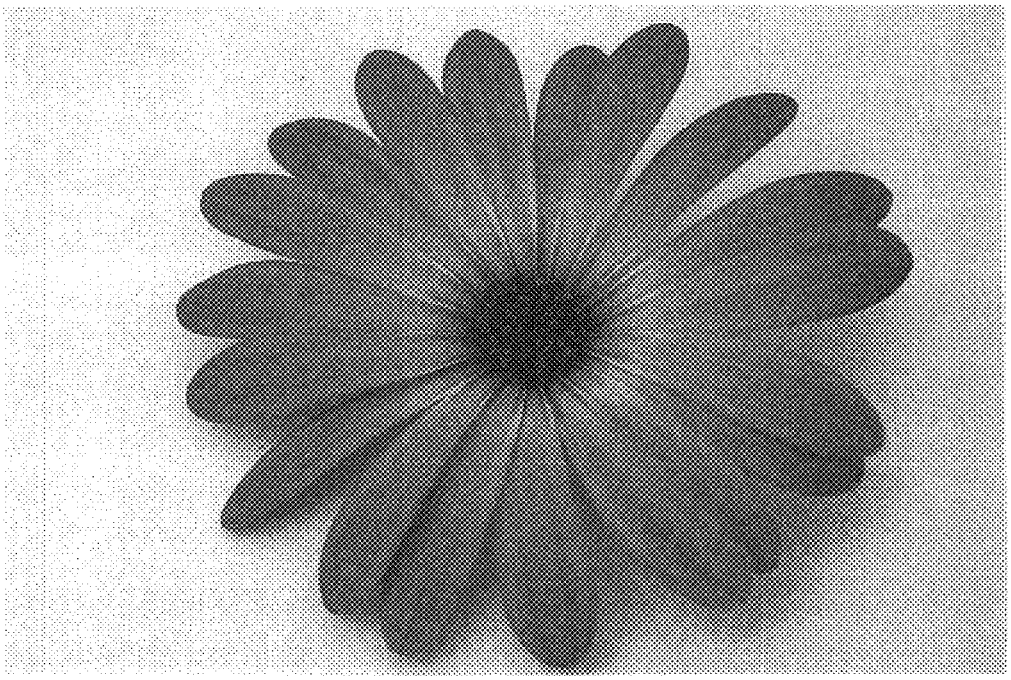
FIG. 2 illustrates a close-up view of individual inflorescences of the new cultivar showing the change in color as the disc florets mature.

The new cultivar has not been observed under all possible environmental conditions to date. Accordingly, it is possible that the phenotype may vary somewhat with variations in the environment, suth as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 24, 2004 between 1:00 and 3:00 p.m. under natural light conditions.

The following descriptions and measurements describe plants produced from cuttings taken from stock plants and grown in a double polycarbonate covered greenhouse under conditions comparable to those used in commercial practice. The plants were grown at West Chicago. Ill. in 10 cm pots for 14 weeks while utilizing a soilless growth medium. Greenhouse temperatures were maintained at approximately 60°–75° F. (15°–24° C.) during the day and approximately 45°–55° F. (7°–13° C.) during the night. Greenhouse light levels were maintained at 5,000 to 9,000 footcandles during the day.

Botanical classification: *Osteospermum ecklonis* cultivar Balserpink.

Parentage: Open pollination of the *Osteospermum ecklonis* commercial variety 'Mira', U.S. Plant Pat. No. 11,082.

Propagation:

*Type cutting.*—Terminal stem.

*Time to initiate roots.*—Approximately 9 to 12 days.

*Time to produce a rooted cutting.*—Approxumately 21 to 28 days.

*Root description.*—Fine, fibrous.

*Rooting habit.*—Freely branching.

Plant description:

*Crop time.*—Approximately 10–13 weeks from a rooted cutting in a 10 cm pot.

*Growth habit.*—Compact, freely branching.

*Form.*—Upright.

*Size.*—Height: Approximately 29.3 cm from soil level to top of plant plane. Width (area of spread) — Approximately 27.4 cm.

*Branch.*—Quantity per plant: Approximately 4. Strength: Strong. Length from soil level to base of peduncle: Approximately 24.3 cm. Diameter: Approximately 4.7 mm. Internode length at middle of branch: Approximately 1.2 cm. Texture: Glabrous, becomes woody with age. Color: N144D with overlay of 187C.

*Foliage.*—Quantity per branch: Approximately 28. Type: Simple. Fragrance: Faint, pungent. Arrangement: Alternate. Aspect: At an acute angle to the stem. Shape: Elliptic. Apex: Acute. Base: Decurrent. Margin: Widely dentate. Venation pattern: Pinnate. Length: Approximately 5.8 cm. Width: Approximately 2.6 cm. Texture of upper and lower surfaces: Glabrous with moderate pubescence along margin. Color of upper surface of mature foliage: Closest to 137A with venation of 145B. Color of lower surface of mature foliage: Closest to 147A with venation of 145B.

Flowering description:

*Time to first flower.*—Approximately 13 weeks from planting of rooted cutting.

*Flowering habit.*—Freely flowering under outdoor growing conditions with substantially continuous blooming from spring through autumn and year round in greenhouse environment.

*Inflorescence arrangement.*—Solitary, terminal.

*Lastingness of inflorescence.*—Approximately 6–10 days.

Inflorescence description:

*Appearance/type.*—Composite, persistent. Shape: Round. Aspect: Facing upward or outward. Disc and ray florets develop acropetally on a capitulum. Fragrance: None.

*Quantity of inflorescences and buds per plant.*—Approximately 1 inflorescence and 2 buds.

*Size.*—Diameter: Approximately 6.9 cm. Depth: Approximately 2.4 cm.

*Bud.*—Rate of opening: Generally takes 3–6 days for buds to progress from first color to fully open inflorescences. Shape: Elliptic. Diameter: Approximately 1 cm. Depth: Approximately 2.2 cm.

*Ray florets.*—Quantity per inflorescence: Approximately 20, arranged in two whorls. Arrangement: Overlapping. Aspect: Flat to slightly concave. Shape: Ligulate. Apex: Emarginate with three tips. Base: Attenuate. Margin: Entire. Length: Approximately 3.7 cm. Width: Approximately 9 mm. Texture: Glabrous. Color: Upper surface: 74B at tip, 74C in center and 83D at margin and near base when first open and 74B at tip and 75C in center when fully open. Lower surface: 85A with ribs of 86B when first open and when fully open.

*Disc.*—Diameter: Approximately 1.1 cm. Depth: Approximately 5 mm.

*Receptacle.*—Shape: Cone. Diameter: 2.5 mm. Depth: 6 mm. Color: 145D.

*Disc florets.*—Quantity per inflorescence: Approximately 105. Arrangement: Massed in center of inflorescence. Shape: Tubular with five lobes each having an acute apex. Margin: Entire. Length: Approximately 8 mm. Diameter at apex: Approximately 3 mm. Diameter at base: Approximately 1 mm. Texture: Glabrous. Color of immature florets: 99A. Color of mature floret: N78B

*Phyllaries.*—Quantity per inflorescence: Approximately 19. Arrangement: Imbricate. Shape: Ovate. Apex: Acuminate. Base: Truncate. Margin: Entire. Length: Approximately 1.2 cm. Width: Approximately 1.9 mm. Texture of center of inner/upper surface: Glabrous. Texture of center of outer/lower surface: Strigose. Color of center of inner/upper surface: Closest to 144C. Color of center of outer/lower surface: Closest to 144B. Texture of margin: Glabrous, papery. Color of margin: 157B, transparent.

*Peduncle.*—Strength: Strong. Aspect: Erect. Length: Approximately 10.8 cm. Diameter: Approximately 1.7 mm. Texture: Strigose. Color: N144D.

*Reproductive organs.*—Androecium: Present on disc florets only. Stamen quantity: 4. Anther shape: Linear. Anther length: Approximately 2.5 mm. Anther color: N89A. Amount of pollen: Abundant. Pollen color: 17A. Gynoecium: Present on ray and disc florets. There is one pistil per floret. Pistil length: Approximately 5 mm. Stigma shape: Cupped. Stigma length: Approximately 0.5 mm. Stigma color: N89A. Style length: approximately 4 mm. Style color: N155B. Ovary diameter: Approximately 0.5 mm. Ovary color: 145C.

Seed and fruit production: Neither seed nor fruit production has been observed.

Disease and pest resistance: Resistance to pathogens and pests common to *Osteospermums* has not been observed.

What is claimed is:

1. A new and distinct cultivar of *Osteospermum* plant named 'Balserpink', substantially as herein shown and described.

* * * * *